US00PP32142P2

(12) United States Plant Patent
Ryan-Bohac

(10) Patent No.: US PP32,142 P2
(45) Date of Patent: Sep. 1, 2020

(54) SWEETPOTATO PLANT NAMED 'CHARLESTON-163'

(50) Latin Name: ***Ipomoea batatas,* L.**
Varietal Denomination: Charleston-163

(71) Applicant: Janice Ryan-Bohac, North Charleston, SC (US)

(72) Inventor: Janice Ryan-Bohac, North Charleston, SC (US)

( * ) Notice: Subject to any disclaimer, the term of this patent is extended or adjusted under 35 U.S.C. 154(b) by 0 days.

(21) Appl. No.: 16/602,263

(22) Filed: Sep. 3, 2019

(51) Int. Cl.
*A01H 5/00* (2018.01)

(52) U.S. Cl.
USPC ..... Plt./258

(58) Field of Classification Search
USPC ..... Plt./258
CPC ..... A01H 5/00
See application file for complete search history.

(56) References Cited

U.S. PATENT DOCUMENTS

PP17,976 P2 9/2007 Sizemore et al.

OTHER PUBLICATIONS

CIP, AVRDC, IBPGR, Descriptors for Sweet Potato (Z. Huaman, ed., International Board for Plant Genetic Resources 1991).
Steed et al., Continuous Flow Microwave-Assisted Processing and Aseptic Packaging of Purple-Fleshed Sweetpotato Purees, 73:9 Journal of Food Science 455-462 (2008).

*Primary Examiner* — Annette H Para
(74) *Attorney, Agent, or Firm* — Koenig IP Works, PLLC

(57) ABSTRACT

A new and distinct cultivar of sweetpotato plant named 'Charleston-163', characterized by high anthocyanin content, high yield, with storage roots having smooth dark purple skin and medium purple flesh. When baked the storage roots have a deep violet color and a unique, sweet flavor with a dry, smooth texture. Storage roots have a long shelf life and will remain marketable up to one year in storage. The new cultivar 'Charleston-163' has field resistance to common soil insects and diseases and a wide adaptation for production in the southeastern United States and California.

6 Drawing Sheets

Genus and species: *Ipomoea batatas*, L.
Cultivar denomination: 'Charleston-163'.

CROSS-REFERENCE TO RELATED APPLICATIONS n/a

ACKNOWLEDGEMENT OF FEDERAL RESEARCH SUPPORT n/a

BACKGROUND OF THE NEW CULTIVAR

The present invention relates to a new and distinct cultivar of sweetpotato, botanically known as *Ipomoea batatas*, and hereinafter referred to by the name 'Charleston-163'. *Ipomoea batatas* is a member of Convolvulaceae. Sweetpotato is the seventh largest crop worldwide and is a major food staple in many countries, mostly in the tropics and semi-tropics. The most popular type of sweetpotato in the United States is the sweet vegetable type with dark copper-rose skin and dark orange, moist flesh. These type of vegetable sweetpotatoes are sweet, syrupy, and strong in flavor. In contrast, the popular sweetpotato varieties in Asia, Africa, and the Caribbean have dry white or yellow flesh, and are bland and starchy. In addition to these types, there are a few rare genotypes with purple flesh. These purple-fleshed types are high in purple pigments called anthocyanins.

Anthocyanins are thought to convey many advantageous health effects, such as strong radical scavenging activity, anti-mutagenic activity, anti-inflammatory activity, antimicrobial activity, ultraviolet light protection, reduction in memory impairment, reduction in high blood pressure, and a reduction in injury to the liver.

There is a great potential to use purple-fleshed sweetpotatoes, such as the 'Charleston-163' cultivar, for a number of processed products. Japanese-bred purple-fleshed sweetpotato cultivars such as 'Yamaga wamurasaki' (commercial cultivar, not patented) are utilized in a number of processed commercial products including natural food colorants, purple paste and flour to use in juices, bread, noodles, jams, confectionary, and fermented beverages. Additionally, purple-fleshed sweetpotatoes may be converted into frozen and aseptic purees for various food applications.

However, many known purple-fleshed varieties have shortcomings. Heirloom purple-fleshed varieties such as 'Okinawa Purple' (commercial cultivar, not patented), which have a tan skin and purple flesh, and Camote morado from Guatemala, do not produce sufficient yields, shape well, or perform well when field grown in the southeastern United States and California. Further, varieties such as 'Stokes Purple' (U.S. Plant Pat. No. 17,976), a purple-skinned, purple-fleshed variety from Asia, does not typically have a uniform root shape and often presents with prominent veins.

The new sweetpotato cultivar 'Charleston-163' is a product of conventional breeding. The female parent, an heirloom cultivar Camote morado from Guatemala (plant introduction (PI) 399163), was open-pollinated by an unknown male parent from breeding line from the Applicant's Charleston sweetpotato breeding program. The stated cross was made in the fall of 2010 through bee-mediated pollination, where the Camote morado parent grew adjacent to a plant bed including hundreds of breeding lines. The seed from the cross was collected in fall of 2010 and planted in the greenhouse that winter, and then transplanted into a seedling trial during the spring of 2011. One individual seedling with purple skin and flesh was selected in fall of 2011 and was designated 'Charleston-163'. Since the Camote morado, like all sweetpotatoes, does not self pollinate, the crosses resulting in seed are considered an open pollination to any of the potential breeding lines in the plant beds. The seed was collected from the Camote morado female parent in the fall of 2010, germinated in spring of 2011, and transplanted into field beds in Colleton County, S.C. The individual seedlings were evaluated in the fall of 2011. One seedling with beautiful purple skin and purple flesh was selected and subjected to cooking and storage tests. From that time forward, 'Charleston-163' was cloned from one seedling and continued to be designated 'Charleston-163'. After multi-year field trials, it was made part of the breeding program's permanent collection.

Asexual propagation of the new sweetpotato cultivar 'Charleston-163' by vegetative cuttings in a controlled environment and plant beds in Colleton County, S.C., since 2011 has shown that the unique features of this new sweetpotato cultivar are stable and reproduce true to type in successive generations.

Plant Breeder's Rights for this cultivar have not been applied for. The new sweetpotato cultivar 'Charleston-163' has not been made publicly available more than one year prior to the filing of this application.

SUMMARY OF THE INVENTION

The new sweetpotato cultivar 'Charleston-163' has not been observed under all possible environmental conditions. The phenotype of the new cultivar may vary with variations in environment and cultural practices such as temperature, light intensity, fertilization, irrigation, and application of plant growth regulators without any change in genotype.

The following traits have been repeatedly observed and are determined to be the unique characteristic of the new sweetpotato cultivar. These characteristics in combination distinguish 'Charleston-163' as a new and distinct cultivar of sweetpotato:

1. high anthocyanin content;
2. high yield;
3. storage roots having sweet and delicious flavor and flesh with dry, smooth texture;
4. long shelf life of storage roots in storage;
5. uniformly shaped storage roots;
6. storage roots with purple flesh and smooth dark purple skin;
7. field resistance to common soil insects and diseases;
8. adapted for production in California and the southeastern United States, such as South Carolina, Georgia, and Florida (for example, USDA Plant Hardiness Zones 8-10).

Plants of the new sweetpotato cultivar 'Charleseton-163' differ from plants of the female parent, Camote morado, in that 'Charleston-163' produces a greater yield and larger storage roots than Camote morado. Formation of uniform U.S. No. 1 and Jumbo sized roots by 'Charleston-163' contribute to high yield in 120 to 130 days after planting. U.S. No. 1 sweetpotatoes are defined by the United States Department of Agriculture (USDA) as firm, smooth, well-shaped storage roots that are free from damage by disease, cuts, freezing, and the like. These roots will have a minimum diameter of not less than 1.75 in and a maximum diameter of not more than 3.5 in. Length will be no less than 3 in and no more than 9 in. Individual root weight will be not more than 20 oz. Under USDA standards, Jumbo sweetpotatoes are larger than U.S. No. 1 sweetpotatoes and individual roots will weigh more than 20 oz. In contrast, under many years of observation in the United States, it was found that the purple female parent, Camote morado, produces only fingerlings, which are roots that have a diameter of less than 1 in and a length of less than 2 in. This contributes to very low yield potential in Camote morado.

Plants of the new sweetpotato cultivar 'Charleseton-163' can be compared to the only other widely available purple sweetpotato, 'Stokes Purple'. In general, plants of the new sweetpotato cultivar 'Charleteston-163' differed from plants of 'Stokes Purple' in the following characteristics:

1. 'Charleston-163' storage roots have uniform shape;
2. 'Charleston-163' lacks prominent veins running on storage root surface skin and cortex; and
3. the attractive flesh of 'Charleston-163' is medium purple with less white mottling than 'Stokes Purple'.

DESCRIPTION OF THE FIGURES

The accompanying photographs (as shown in FIGS. 1-6) illustrate the overall appearance of the new sweetpotato cultivar 'Charleston-163'. These photographs show the colors as true as can be reasonably obtained in colored reproductions of this type. Colors in the photographs may differ slightly from the color values cited in the detailed botanical description, which accurately describe the colors of the new sweetpotato cultivar.

DETAILED BOTANICAL DESCRIPTION OF THE CULTIVAR

Figure 1:
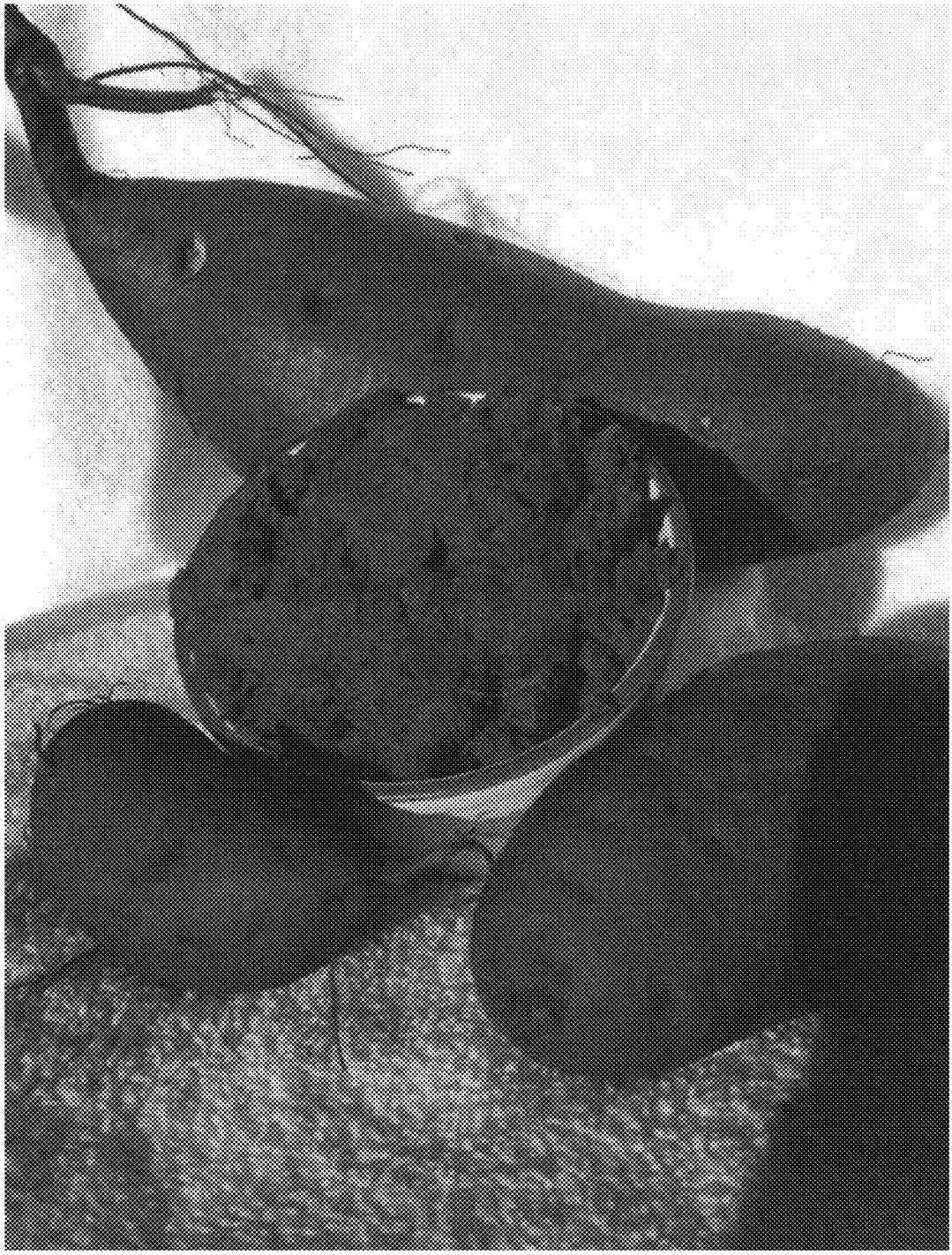
FIG. 1 shows storage roots of the new sweetpotato cultivar 'Charleston-163' as well as a bowl of baked, mashed flesh to show the color and consistency.
Figure 2:
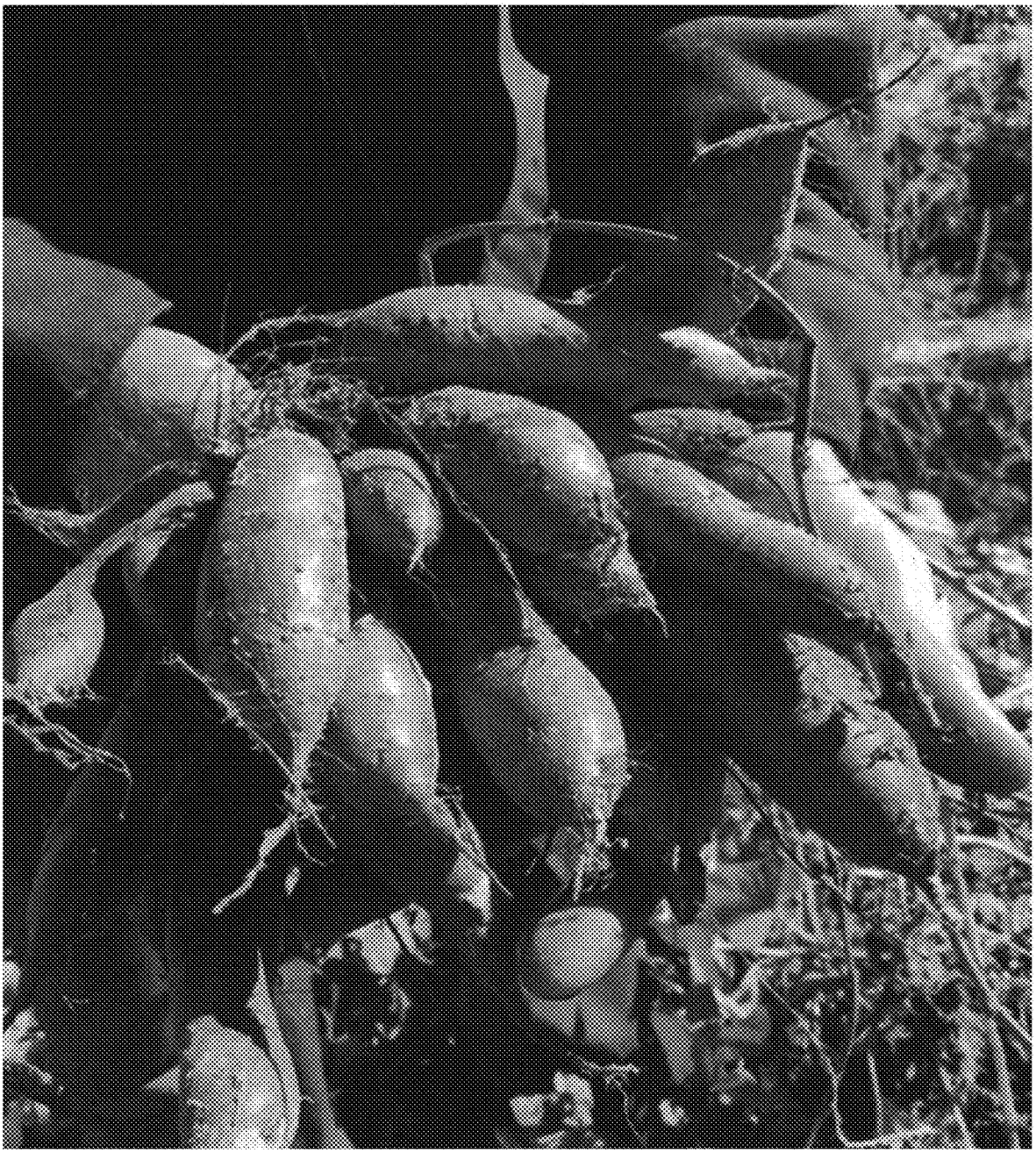
FIG. 2 shows a single plant of the new sweetpotato cultivar 'Charleston-163' having sixteen storage roots (petite and fingerling size)
Figure 3:
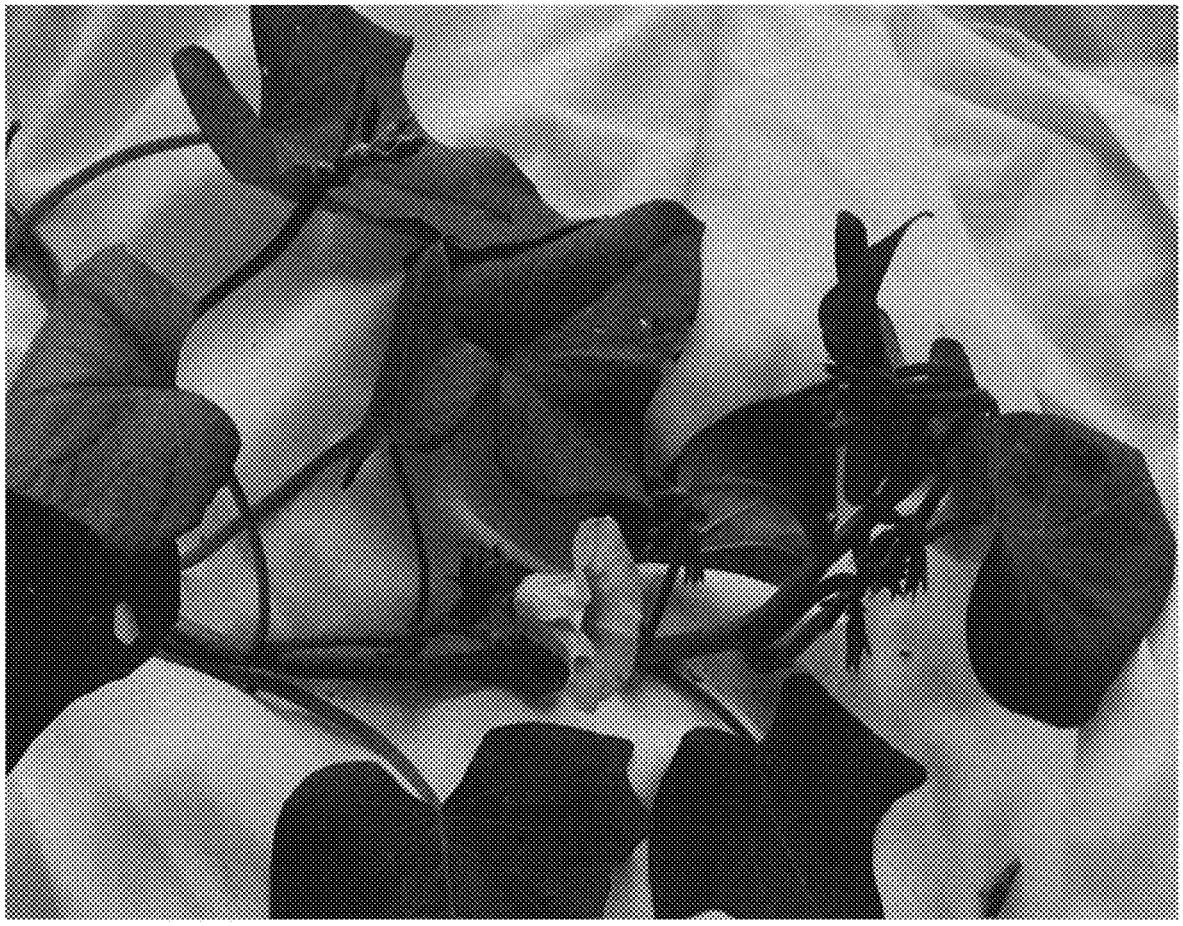
FIG. 3 shows a flower and upper surfaces of leaves attached to a stem of a main plant of the new sweetpotato cultivar 'Charleston-163'.
Figure 4:
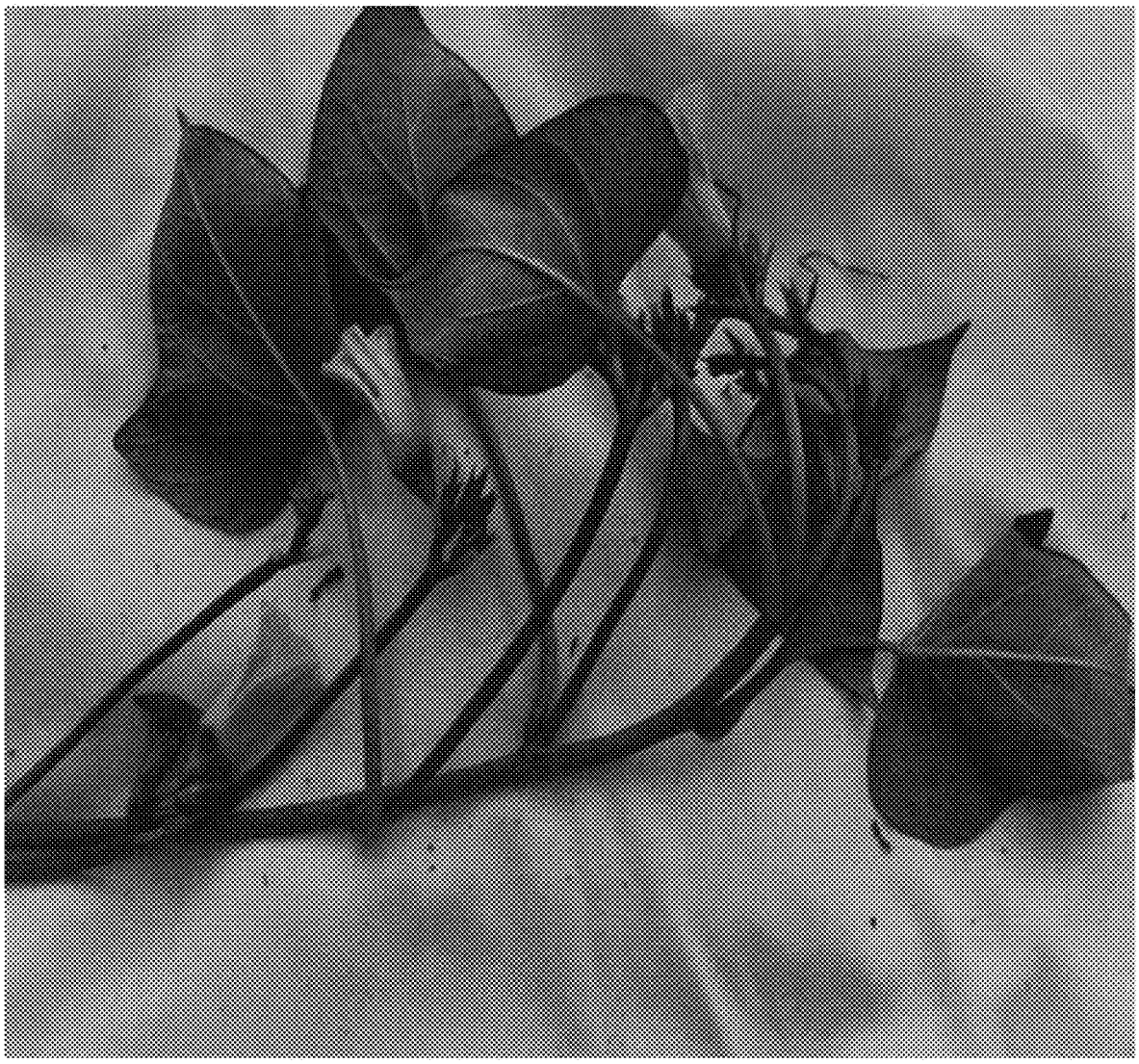
FIG. 4 shows flowers and lower surfaces of leaves attached to a stem of a main plant of the new sweetpotato cultivar 'Charleston-163' (with the cyme structure of the flower shown)
Figure 5:
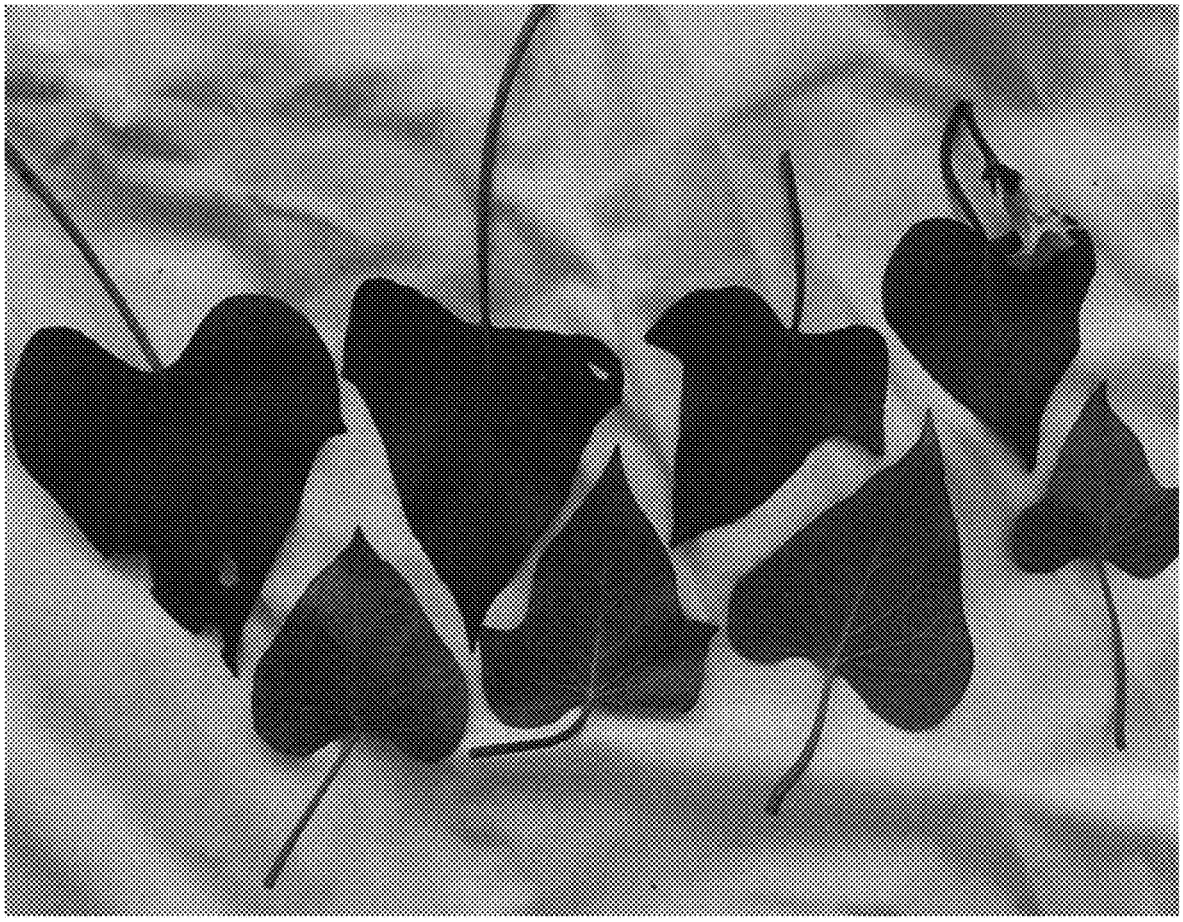
FIG. 5 shows a flower and upper surfaces (top row) and lower surfaces (bottom row) of leaves detached from a stem of the main plant of the new sweetpotato cultivar 'Charleston-163'.
Figure 6:
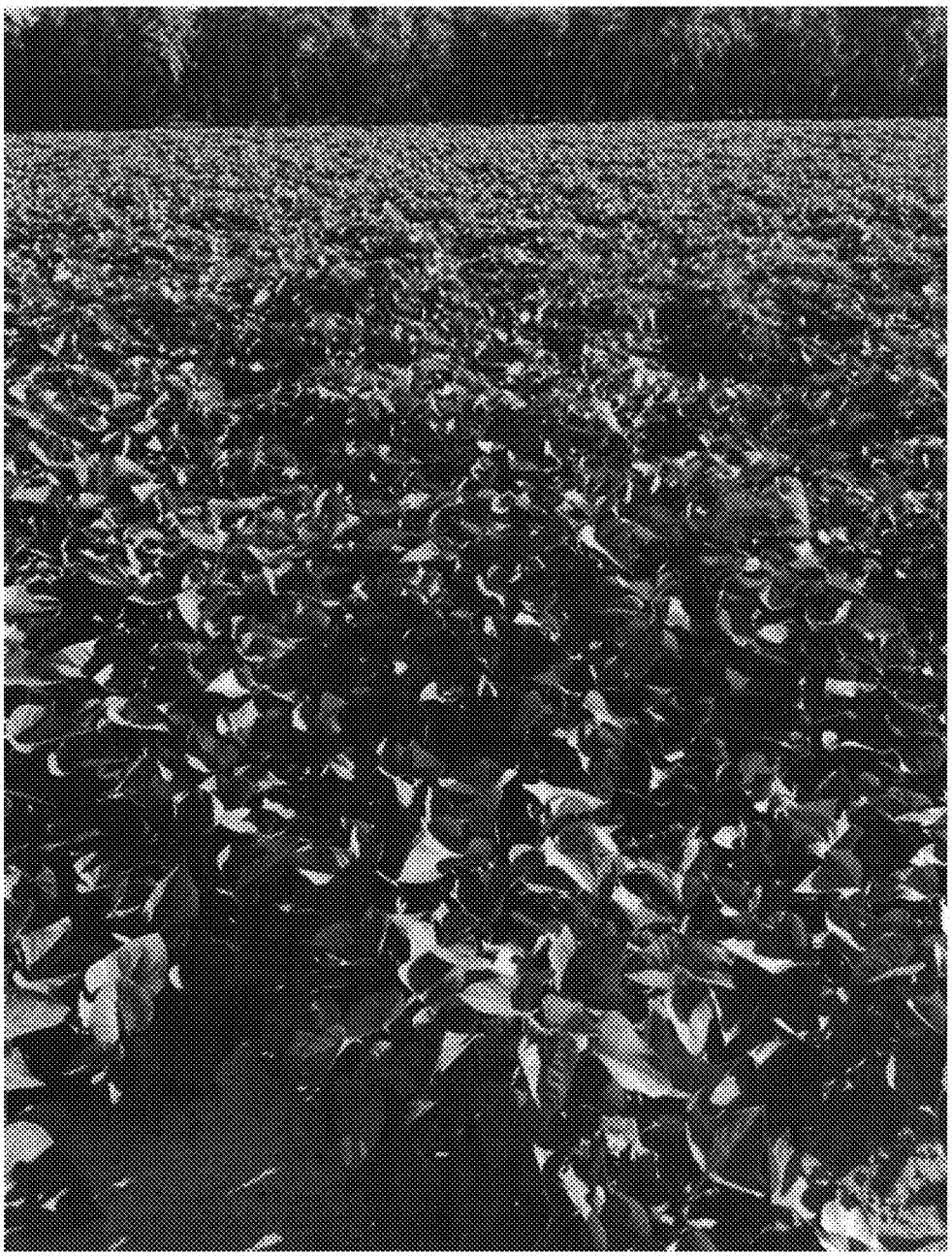
FIG. 6 shows a field of plants of the new sweetpotato cultivar 'Charleston-163', grown organically, in Livingston, Calif.

In the following description, color references are made to the Munsell Book of Color, Matte Finish Collection, 1976 Edition, except where general terms of ordinary dictionary significance are used.

DESCRIPTION OF GROWING CONDITIONS

Plants of the new sweetpotato cultivar 'Charleston-163' used for the description herein were planted in May and harvested between 120 and 140 days after planting, and were grown using standard growing conditions and fertilization. In all trials on sweetpotato farms in Colleton County, S.C., Hastings, Fla., and Merced County, Calif., it was found that the new cultivar performed well on local sandy loam soils low in organic matter. Soil samples were submitted for soil testing, and in South Carolina, the field was fertilized according to recommendations for sweetpotato production (90 lbs of nitrogen, 110 lbs of phosphorus, and 110 lbs. of potash) using a split fertilization, with half applied at planting and half applied at about 45 to 50 days after planting. Further, micro nutrients were applied based on test results for production of sweetpotato in South Carolina, which recommended a micronutrient composition of 5 lbs of sulfur, 0.38 lbs of boron, and 10 lbs of manganese. At California and Florida locations, 90 lbs per acre of nitrogen, phosphorus, and potassium were applied according to recommendations based on local soil tests.

To control weeds, 1.5 pints per acre of a pre-emergent herbicide were applied at 2-10 days after transplanting, as well as a grass herbicide at 1 pint per acre. No fungicides, nematicides, or insecticides for soil insect pests were required. In trials in South Carolina and California, it appears that the new cultivar is as field resistant and/or tolerant to soil pathogens and insect pests and diseases as the female parent Camote morado, even though 'Charleston-163' was not subjected to screening under standard conditions. Such pests and diseases include bacterial root rot, bacterial stem rot, *Fusarium* root rot, WDS complex (involving wireworms, *Canoderus* spp.; cucumber beetles, *Diabrotica* spp.; and flea beetles, *Systena* spp.; as well as, in some cases, beetles such as the flea beetle (*Chaetocnema confinis*), white grubs (*Plectris aliena*), and/or *Phyllophaga ephilada*). In contrast, the cultivar 'Covington' (commercial cultivar, not patented) grown in the same fields as 'Charleston-163' showed damage to these pests and/or diseases. In California trials, plants of the new cultivar were grown under certified organic field conditions with no soil insect pest and/or disease damage observed. In the same field, 'Covington' showed insect damage on the storage roots due to WDS complex and flea beetle.

BOTANICAL DESCRIPTION

Botanical classification:

*Family*.—Convolvulaceae.

*Botanical name*.—*Ipomoea batatas*, (L) Lam.

*Common name*.—Sweetpotato.

*Cultivar*.—'Charleston-163'.

Parentage:

*Female or seed parent*.—Camote morado.

*Male or pollen parent*.—Unknown; open pollination from one of the Charleston, S.C. sweetpotato breeding lines.

Propagation: Asexual reproduction of clones by vine cuttings. Unrooted cuttings having a length of approximately 10 in to 11 in were transplanted 12 in apart with a "finger" transplanter.

Storage root description:

*Color, skin*.—Dark purple/scarlet (2.5RP (Red Purple) 3/2).

*Color, flesh*.—Raw: Purple (5R (Red) P (Purple) 3/6) with very small amounts of white.

*Color, flesh*.—Cooked: Uniformly distributed, vivid violet.

*Rooting habit*.—Adventitious roots with some developing into storage roots.

*Storage root size and shape*.—Small to medium: Roots having a diameter of between approximately 1.5 in and approximately 2.25 in and a length of between approximately 3 in and approximately 7 in. Elliptic in shape. Medium to large: Roots having a diameter of between approximately 1.75 in and approximately 3.5 in and a length of between approximately 3 in and approximately 9 in. Ovate or elliptic in shape.

Plant description:

*Type*.—Herbaceous vine, can be perennial or annual.

*Plant form*.—Trailing herbaceous vine.

*Growth habit*.—Annual, non-determinate, moderately to rapidly spreading.

*Plant height*.—Rarely taller than 2 feet in height.

*Stem color*.—Green (G (Green) lOGY 6/1) specked with medium purple (2.5R (Red) P (Purple) 3/2).

Foliage description:

*Arrangement*.—Alternate.

*Shape*.—Triangular to tri-lobed.

*Margin*.—Entire to slightly toothed.

*Texture, upper and lower surfaces*.—Coarse.

*Color, developing and fully expanded foliage*.—Upper surface, expanded: Medium green (7.5G (Green Yellow) 4/4) with green veins. Lower surface, expanded: Medium green (7.5G (Green) Y (Yellow) 6/4).

*Petiole*.—Length: Approximately 4 in. Color: Green (G (Green) 10GY 6/1).

Inflorescence description: Unlike most commercial sweetpotato cultivars that bloom only on short days, 'Charleston-163' is day-length neutral and produces many flowers throughout both long days of summer and shorter days of fall. 'Charleston-163' starts blooming in late May or early June, and blooms until frost. In contrast, it was reported that 'Stokes Purple' blooms for only about 60 days.

*Flower type*.—Cyme.

*Flowering habit*.—Peduncle typically bears 3 to 5 flowers, sometimes bearing a single flower, with each flower having a height of approximately 3 cm. The flower opens in the morning and usually closes by evening. The flower does not have a fragrance. Number of flowers per inflorescence: 3 to 5 flowers, sometimes a single flower.

*Flower appearance*.—Tubular or funnel-shaped with 5 fused petals. The flowers are complete with a white stigma and having approximately 5 white anthers (2 anthers, each approximately 2 cm in length, and 3 short anthers, each being approximately 1.5 cm in length). The stigma is approximately 2.5 cm long and is exerted longer than the longest anther.

*Corolla*.—Arrangement/appearance: Petals (typically 5) are fused into a tube or funnel, limb or top of corolla has round or rotate shape. In contrast, the top of the corolla of the flower of 'Stokes Purple' has a semi-stellate shape. Tube color (mature): Outer surface: Lavender (10P 9/11). Inner surface/throat: Dark purple (7.5R (Red) P (Purple) 4/6).

*Peduncle*.—The peduncle is approximately 5 cm long and is the same green color as the stem (green (10GY6/1)).

*Calyx*.—The calyx includes 5 sepals, three of which are obovate in shape, with 2 inner sepals having a length of approximately 1 cm and 2 sepals having a length of approximately 0.75 in and being lanceolate in shape.

COMPARISON WITH KNOWN CULTIVARS

'Stokes Purple' (U.S. Plant Pat. No. 17,976), a purple-skinned, purple-fleshed variety from Asia, is currently the only purple sweetpotato available in several states. 'Stokes Purple' does not typically have a uniform root shape, is often long and lumpy in shape, and often presents with prominent veins on the surface of the skin of the storage roots. In contrast, 'Charleston-163' produces uniformly shaped storage roots that are elliptical in shape, lacks prominent veins, and has flesh that is medium purple with less white mottling than 'Stokes Purple'.

'Okinawa Purple' (heirloom cultivar, not patented), a tan-skinned, purple-fleshed variety from Asia, does not produce sufficient yields, shape well, or perform well when field grown in the southeastern United States and California. In contrast, 'Charleston-163' has purple skin, purple flesh, produces sufficient yield, produces uniformly shaped storage roots, and is adapted for production in California and the southeastern United States.

I claim:

1. A new and distinct sweetpotato plant named 'Charleston-163' as illustrated and described herein.

* * * * *